(12) United States Patent
Lee et al.

(10) Patent No.: US 12,042,137 B2
(45) Date of Patent: Jul. 23, 2024

(54) TISSUE RETRACTION DEVICES, SYSTEMS, AND METHODS

(71) Applicant: Boston Scientific Scimed, Inc., Maple Grove, MN (US)

(72) Inventors: Danny Lee, Cambridge, MA (US); John Unger, Wrentham, MA (US); Anne Sluti, Watertown, MA (US); Kathleen M. Laliberte, Littleton, MA (US); Talha Riaz, Framingham, MA (US); Tracy Andreotti, Milford, MA (US); Routha Sim, Lowell, MA (US); Juan C. Rodriguez Salazar, Watertown, MA (US); Caroline Riedel, Westford, MA (US); Jose L. Garcia-Cordero, Ocala, FL (US); Ryan V. Wales, Northborough, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 236 days.

(21) Appl. No.: 17/108,531

(22) Filed: Dec. 1, 2020

(65) Prior Publication Data
US 2021/0169464 A1    Jun. 10, 2021

Related U.S. Application Data

(60) Provisional application No. 62/943,885, filed on Dec. 5, 2019.

(51) Int. Cl.
*A61B 17/02* (2006.01)
*A61B 17/08* (2006.01)
(Continued)

(52) U.S. Cl.
CPC ........ *A61B 17/0218* (2013.01); *A61B 17/083* (2013.01); *A61B 2017/00269* (2013.01);
(Continued)

(58) Field of Classification Search
CPC .............................. A61B 17/083; A61B 17/088
See application file for complete search history.

(56) References Cited

U.S. PATENT DOCUMENTS

| 89,551 A * | 5/1869 | Brunner ................ A01M 23/24 43/86 |
| 5,582,577 A * | 12/1996 | Lund .................. A61B 17/0218 600/233 |

(Continued)

FOREIGN PATENT DOCUMENTS

| CN | 109620320 A | 4/2019 |
| CN | 209611212 U | 11/2019 |

(Continued)

OTHER PUBLICATIONS

International Search Report and Written Opinion for the International Patent Application No. PCT/US2020/062691, mailed Apr. 8, 2021, 12 pages.

(Continued)

*Primary Examiner* — Nicholas W Woodall
(74) *Attorney, Agent, or Firm* — Seager, Tufte & Wickhem, LLP

(57) ABSTRACT

The present disclosure relates generally to the field of medical devices. In particular, the present disclosure relates to a tissue traction device, e.g., for endoscopic tissue dissection. For example, a tissue traction device may include a first clip comprising opposable jaws. The device may include a traction band having a first end, a second end, a length therebetween and extending along a longitudinal axis. The band may have a first aperture at the first end. A second aperture may be at the second end of the band. A first jaw of the opposable jaws of the first clip may be disposed through the first aperture.

20 Claims, 11 Drawing Sheets

(51) Int. Cl.
  *A61B 17/00* (2006.01)
  *A61B 17/11* (2006.01)
  *A61B 17/32* (2006.01)
  *A61M 13/00* (2006.01)

(52) U.S. Cl.
  CPC ........... *A61B 2017/0034* (2013.01); *A61B 2017/0287* (2013.01); *A61B 2017/1103* (2013.01); *A61B 17/320016* (2013.01); *A61M 13/003* (2013.01)

(56) References Cited

U.S. PATENT DOCUMENTS

| | | | | |
|---|---|---|---|---|
| 5,972,022 | A * | 10/1999 | Huxel | A61F 2/0063 606/215 |
| 7,011,667 | B2 * | 3/2006 | Kobayashi | A61B 17/1285 606/139 |
| 7,335,213 | B1 * | 2/2008 | Hyde | A61B 17/0643 606/151 |
| 9,101,357 | B2 * | 8/2015 | Regner | A61B 17/0643 |
| 10,933,219 | B2 * | 3/2021 | Unger | A61B 1/00087 |
| 10,973,506 | B2 * | 4/2021 | Smith | A61B 17/122 |
| 2010/0204727 | A1 | 8/2010 | Dominguez | A61B 34/70 606/205 |
| 2013/0053745 | A1 | 2/2013 | Kobayashi et al. | |
| 2018/0035997 | A1 * | 2/2018 | Smith | A61B 17/1285 |
| 2018/0279869 | A1 | 10/2018 | Wales et al. | |
| 2019/0099172 | A1 * | 4/2019 | Wales | A61B 17/29 |
| 2019/0133591 | A1 | 5/2019 | Dobashi et al. | |
| 2019/0336728 | A1 | 11/2019 | Unger et al. | |
| 2021/0068805 | A1 * | 3/2021 | Ji | A61B 17/0218 |

FOREIGN PATENT DOCUMENTS

| | | |
|---|---|---|
| EP | 3689254 A1 | 8/2020 |
| JP | 200862004 A | 9/2009 |
| JP | 2011217937 A | 11/2011 |
| JP | 6948637 B2 | 10/2021 |
| WO | 2018027113 A1 | 2/2018 |
| WO | 2020015692 A1 | 1/2020 |

OTHER PUBLICATIONS

Chen et al., "A clinical comparative study of rubber ring versus dental floss combined with hemoclipping assisted endoscopic submucosal dissection on gastrointestinal tumor", J Shanghai Jiao Tong University 37(7):1010-1014 (2017).

Ge et al., "Novel clip-band traction device to facilitate colorectal endoscopic submucosal dissection and defect closure, Tools and Techniques", Tools and Techniques| vol. 5, Issue 5, p. 180-186, May 1, 2020.

Sakamoto N. et al., The Facilitation of a New Traction Device (S-O Clip) Assisting Endoscopic Submucosal Dissection for Superficial Colorectal Neoplasms, Endoscopy 2008; 40:E94-95.

Fujii, T et al., A Novel Endoscopic Suturing Technique Using a Specialty Designed So-Called "8-Ring" in Combination With Resolution Clips (With Videos), Gastrointestinal Endoscopy 2007; 66(6):1215-1220.

Matsumoto K. et al., T1594 a New Traction Device for Gastric Endoscopic Submucosal Dissection (ES): Two-Point Fixed by Latex Traction for Early Gastric Cancer, Gastrointestinal Endoscopy, 71(5): AB317 (2010).

Imaeda, H. et al., Advanced Endoscopic Submucosal Dissection with Traction, World Journal of Gastrointestinal Endoscopy 6(7):286-295 (2014).

Sakamoto, N. et al., "Loop Clip' a new closure device for large mucosal defects after EMR and ESD", Endoscopy 40:E97-E98 (2008).

Mori H, et al., The "Loop Clip" Is Useful For Closing Large Mucosal Defects After Colorectal Endoscopic Submucosal Dissection a Preliminary Clinical Study, Digestive Endoscopy 2011; 23:330-331.

Takeda T et al., Traction Device to Remove an Adenoma in the Appendiceal Orifice by Endoscopic Submucosal Dissection, Endoscopy 2013; 45:E239-E240.

* cited by examiner

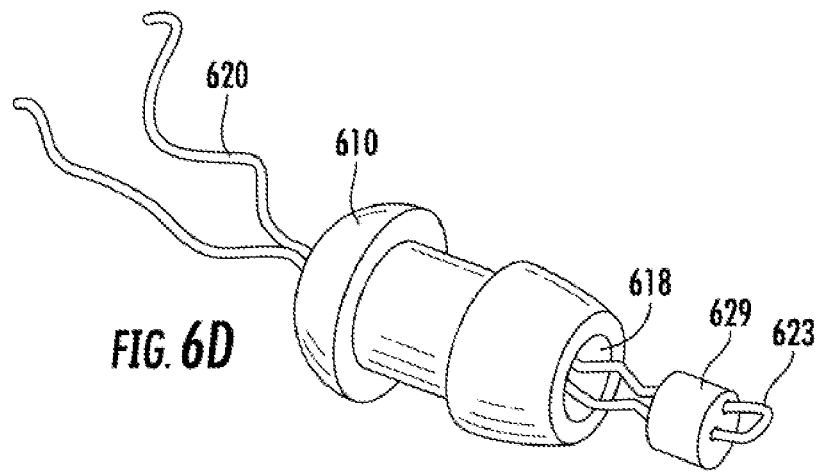
FIG. 6D
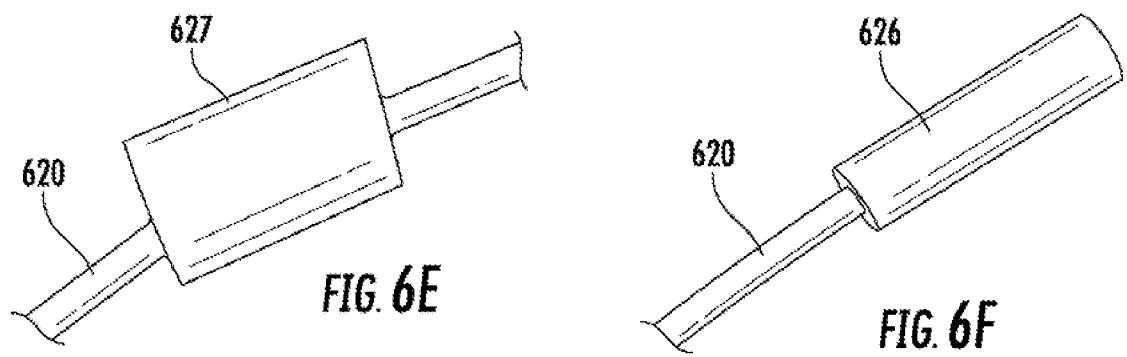
FIG. 6E
FIG. 6F
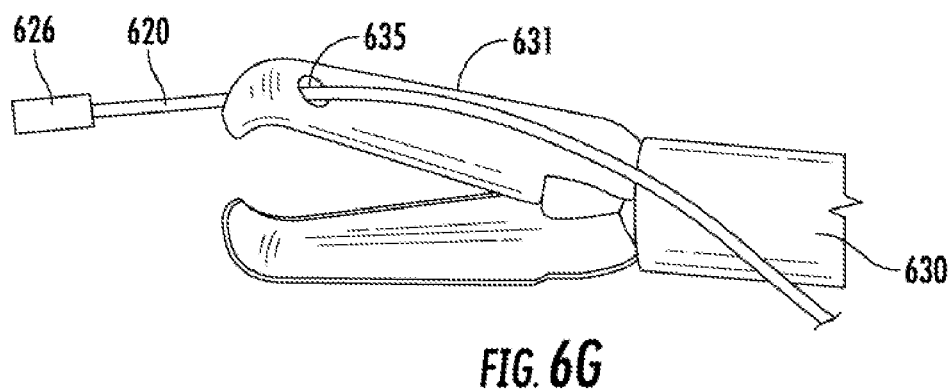
FIG. 6G

TISSUE RETRACTION DEVICES, SYSTEMS, AND METHODS

CROSS-REFERENCE TO RELATED APPLICATIONS

The present application claims the benefit of priority under 35 U.S.C. § 119 to U.S. Provisional patent Application 62/943,885, filed Dec. 5, 2019, which application is incorporated herein by reference in its entirety for all purposes.

FIELD

The present disclosure relates generally to the field of medical devices. In particular, the present disclosure relates to tissue traction devices, e.g., for endoscopic procedures such as tissue dissection, and related methods of use thereof.

BACKGROUND

Accurately and efficiently performing an endoscopic tissue resection/dissection procedure includes the ability to maintain traction as the boundaries of the target tissue are dissected. Traction systems may be unable to maintain or adjust tension applied to the target tissue, possibly obstructing a medical professional's view of the target tissue and/or interfering with accessory tools. These complications may directly contribute to increased procedures time, complexity, and risk of perforation or bleeding.

It is with these considerations in mind that the improvements in the tissue traction devices and related methods of use of the present disclosure may be useful.

SUMMARY

The present disclosure, in its various aspects, is directed generally to medical devices, and more specifically to tissue traction devices, traction methods, and related delivery systems. Embodiments according to the present disclosure, including as described herein, may decrease complications around tissue resection procedures, such as visualization, procedure time, and procedure complexity. In an aspect, a tissue traction device may include a first clip comprising opposable jaws. The device may include a traction band having a first end, a second end, a length therebetween and extending along a longitudinal axis. The band may have a first aperture at the first end. A second aperture may be at the second end of the band. A first jaw of the opposable jaws of the first clip may be disposed through the first aperture.

In various embodiments described here or otherwise, the second aperture may extend along the longitudinal axis toward the first aperture. The second aperture may have a diameter that is larger than an outer diameter of the first end of the traction band. The second end of the traction band may be extendable away from a second jaw of the opposable jaws in a deployed configuration. A third aperture maybe along the traction band between the first aperture and the second aperture. A second clip may be at least partially disposable through the second aperture. The first jaw of the first clip may include a wall extending substantially radially from the first jaw adjacent the traction band.

In an aspect, a tissue traction device may include a traction band having a first end, a second end, a length therebetween and extending along a longitudinal axis. A first connector body may be coupled to the first end of the traction band, and a second connector body coupled to the second end of the traction band. A first filament may extend from the first connector body and away from the traction band, and a second filament extending from the second connector body and away from the traction band. A loop may be formed at each filament.

In various embodiments described here or otherwise, one of the first connector body or the second connector body may further comprise a lumen and one of the filaments extends within the lumen. A rod may reversibly extendable within the lumen configured to couple the filament to one of the first connector body and the second connector body. The filament may include a midportion extendable within the lumen and two ends comprising loops extendable out of the lumen. A first loop of the filament may be configured to be engaged by a clip and anchored to a tissue, and wherein a second loop of the filament is configured to be pulled to release the filament from one of the first connector body and the second connector body. The midportion may be coupled to an anchoring element within the lumen. An overtube may be disposed about the traction band. One of the filaments may extend through an aperture of filament having a bulbous portion having a width that is longer than the aperture.

In an aspect, a method of resecting a target tissue may include coupling a first end of a traction band to the target tissue. A second end of the traction band may be coupled to another tissue. A body lumen comprising the target tissue may be insufflated thereby increasing a tension in the traction band. The target tissue may be resected.

In various embodiments described here or otherwise, the body lumen may be suctioned thereby decreasing a distance between the target tissue and the other tissue. The body lumen may be ventilated thereby decreasing a distance between the target tissue and the other tissue. A midportion of the traction band may be coupled to a third tissue. The traction band may be released from the other tissue.

BRIEF DESCRIPTION OF THE DRAWINGS

Non-limiting embodiments of the present disclosure are described by way of example with reference to the accompanying figures, which are schematic and not intended to be drawn to scale. For example, devices may be enlarged so that detail is discernable, but is intended to be scaled down in relation to, e.g., fit within a working channel of a delivery catheter or endoscope. In the figures, each identical or nearly identical component illustrated is typically represented by a single numeral. For purposes of clarity, not every component is labeled in every figure, nor is every component of each embodiment shown where illustration is not necessary to allow those of ordinary skill in the art to understand the disclosure. In the figures:

FIG. 6D illustrates a filament extending from a connector body and coupled to an anchoring element, in accordance with an embodiment of the present disclosure.

FIG. 6E illustrates a shaft crimped to a filament, in accordance with an embodiment of the present disclosure.

FIG. 6F illustrates a heat-formed bulbous portion of a filament, in accordance with an embodiment of the present disclosure.

FIG. 6G illustrates a filament extending through an aperture of a jaw of a clip, in accordance with an embodiment of the present disclosure.

Figure 1:
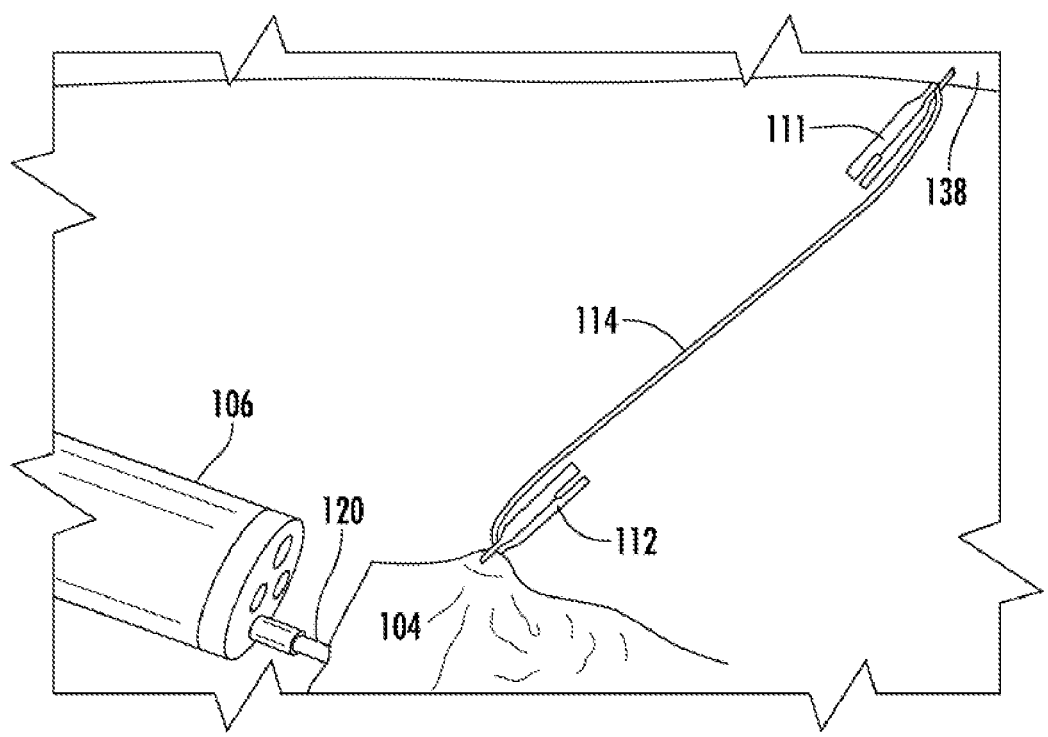
FIG. 1 illustrates a tissue traction device deployed in a body lumen, according to an embodiment of the present disclosure.

It is noted that the drawings are intended to depict only typical or exemplary embodiments of the disclosure. Accordingly, the drawings should not be considered as limiting the scope of the disclosure. The disclosure will now be described in greater detail with reference to the accompanying drawings.

DETAILED DESCRIPTION

As used herein, "proximal end" refers to the end of a device that lies closest to the medical professional along the device when introducing the device into a patient, and "distal end" refers to the end of a device or object that lies furthest from the medical professional along the device during implantation, positioning, or delivery.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used in connection with other embodiments whether or not explicitly described unless clearly stated to the contrary.

All numeric values are herein assumed to be modified by the term "about," whether or not explicitly indicated. The term "about", in the context of numeric values, generally refers to a range of numbers that one of skill in the art would consider equivalent to the recited value (i.e., having the same function or result). In many instances, the term "about" may include numbers that are rounded to the nearest significant figure. Other uses of the term "about" (i.e., in a context other than numeric values) may be assumed to have their ordinary and customary definition(s), as understood from and consistent with the context of the specification, unless otherwise specified. The recitation of numerical ranges by endpoints includes all numbers within that range, including the endpoints (e.g., 1 to 5 includes 1, 1.5, 2, 2.75, 3, 3.80, 4, and 5).

The detailed description should be read with reference to the drawings, which are not necessarily to scale, depict illustrative embodiments, and are not intended to limit the scope of the invention.

A number of medical procedures, including along the digestive and/or biliary tract, utilize medical devices to access tissue intended for removal (e.g., "target tissue") within the body. For example, in some current medical procedures (e.g., endoscopic submucosal dissection (ESD), endoscopic mucosal resection (EMR), Peroral Endoscopic Myotomy (POEM), cholecystectomy, Video-Assisted Thoracoscopic Surgery (VATS)), physicians may utilize an endoscope or similar medical device to access and remove diseased lesions. Further, as part of such procedures, a physician may utilize an endoscope capable of both accessing the target tissue site while also permitting a resecting device to be deployed therethrough to resect target tissue. Additionally, in some instances, an endoscope may incorporate features which assist the physician in visualizing and performing the tissue dissection/resection procedure. For example, some endoscopes may include a light and/or camera designed to illuminate and/or visualize the body lumen as the endoscope is navigated and positioned adjacent to the target tissue site. Additionally, some endoscopes may also include a lumen (e.g., a working channel) through which a resecting device, grasping member, delivery catheter for the same, or other accessory devices, may be deployed and utilized. Additional visualization methods may be alternatively or additionally employed, e.g., fluoroscopy.

While physicians are becoming more proficient at resecting diseased lesions from within the body (e.g., within the digestive tract, abdominal cavity, thoracic cavity, etc.), present traction methods may continue to be inefficient to the physician. For example, in some instances poor visualization and poor ability to engage and manipulate tissue may result in a prolonged tissue dissection procedure. An aspect of EMR/ESD that may be difficult is the positioning and maneuvering (e.g., traction) of a resected tissue flap during and after resecting. In some EMR/ESD procedures, physicians may use separate devices to provide a means of tissue traction. Such procedures may include multiple device exchanges and extended procedure times. Such systems may be unable to maintain or adjust tension applied to the target tissue, and/or may maintain or adjust tension applied to the target tissue in an inefficient or inconsistent manner.

Referring to FIG. 1, an embodiment of a tissue traction device is illustrated as delivered and applying tension between a target tissue 104 and another tissue portion 138. A traction band 114 is coupled to a first clip 112 at a first end of the traction band 114. The first clip 112 is coupled to the target tissue 104 for resection. A second end of the traction band 114 is coupled to a second clip 111. The second clip 111 is coupled to the other tissue portion 138 such that the traction band 114 is in tension. A resecting tool 120 is delivered toward the target tissue 104 via an endoscope 106. As the target tissue 104 is resected, the traction band 114 pulls the first clip 112 and the target tissue 104 substantially toward the second clip 111 such that visualization between the endoscope 106, the tool 120, and the target tissue 104 is maintained.

Figure 2A:
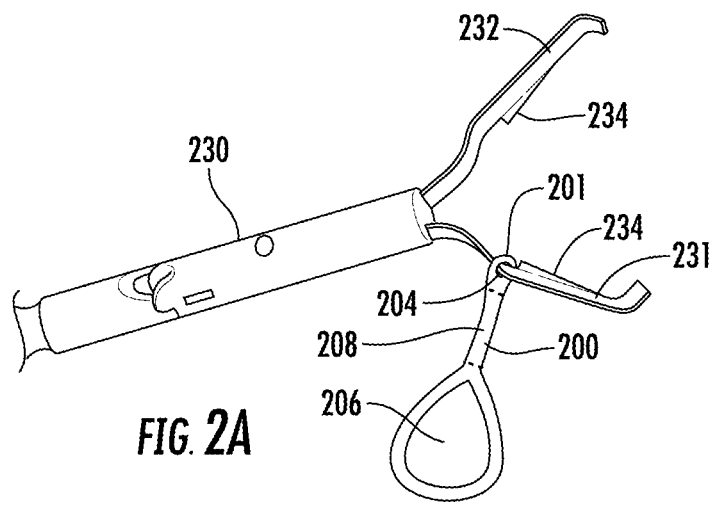
FIG. 2A illustrates a tissue traction device having a traction band disposed on a jaw of a clip, in accordance with an embodiment of the present disclosure.

Referring to FIG. 2A, one example of an embodiment of a traction band 200 according to the present disclosure is illustrated. The traction band 200 has a first end 201, a second end 202, and a length therebetween extending along a longitudinal axis of the traction band 200. The first end 201 includes a first aperture 204. The traction band 200 is coupled to a clip 230. The clip 230 includes first and second opposable jaws 231, 232. In embodiments, the clip 230 may be a single-use hemostasis clip, and in other embodiments, the clip 230 may be a repositionable clip. The first jaw 231 is disposed through the first aperture 204 of the traction band 200. The first aperture 204 has an inner diameter that substantially matches an outer circumference of a portion of the first jaw 231. In some embodiments the inner diameter of the first aperture 204 may be smaller than the outer diameter of the first jaw 231 but may be stretchable to accommodate the first jaw 231. Thus, the traction band 200 may be connected to the first jaw 231 by a friction fit. The jaws 231, 232 include a midportion 234 having a wall extending substantially radially from the jaws 231, 232. The midportion 234 is adjacent to and distal to the first end 201 of the traction band 200. The midportion 234 may assist in preventing translation of the traction band 200 along the first jaw 231. The second end 202 of the traction band 200 includes a second aperture 206. The second aperture 206 has a diameter that is larger than a diameter of the first aperture 204 and is also larger than a width of the first end 201. In embodiments, the diameter of the second aperture 206 may be sized to receive at least a portion of a single-use hemostasis clip and/or a repositionable clip (see FIGS. 2E-2F). The traction band 200 is coupled to the clip 230 such that the second end 202 is extendable away from the jaws 231, 232 by a linear portion 208 extending between the first end 201 and the second aperture 206.

Figure 2B:
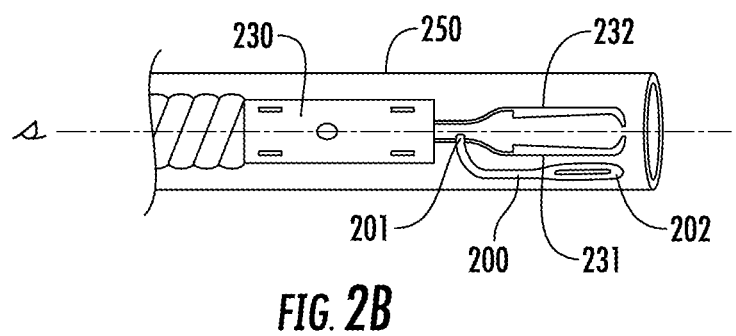
FIG. 2B illustrates the tissue traction device of FIG. 2A disposed within a sheath.

With reference to FIG. 2B, the clip 230 and traction band 200 of FIG. 2A may be loaded into a sheath 250. The traction band 200 is coupled to the first jaw 231 of the clip 230 such that the traction band 200 is extends substantially parallel along and radially farther from an axis $s$ of the sheath 250 than the first jaw 231 is from the axis $s$. The clip 230 is oriented within the sheath 250 such that the jaws 231, 232 and the second end 202 of traction band 200 are oriented distally. The traction band 200 is positioned within the sheath 250 outside of the jaws 231, 232 such that the traction band 200 may not be damaged by the jaws 231, 232. In the orientation depicted in FIG. 2B, the clip 230 and traction band 200 may be translated through the sheath 250 such that the traction band 200 maintains a substantially linear orientation without entanglement. Alternatively, the traction band 200 may be oriented between the jaws 231, 232 within the sheath 250 such that friction between the traction band 200 and the sheath 250 may be reduced.

Figure 2C:
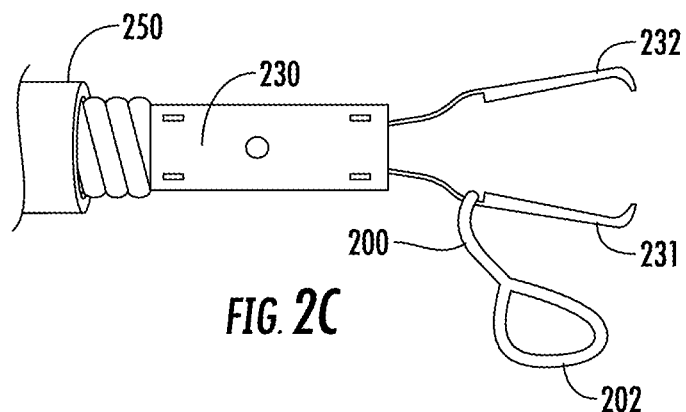
FIG. 2C illustrates the tissue traction device of FIGS. 2A and 2B distal to the sheath of FIG. 2B for delivery.

With reference to FIG. 2C, the sheath 250 is retracted from the clip 230 and traction band 200 and/or the clip 230 and traction band 200 are distally translated out of the sheath 250. In some embodiments, the sheath 250 may remain stationary and the clip 230 and the traction band 200 may be extendable distally. The jaws 231, 232 are oriented distally for engaging tissue and deployment, and the second end 202 of the traction band 200 is oriented away from the jaws 231, 232 such that the second end 202 is visible and does not interfere with operation of or become damaged by the jaws 231, 232.

Figure 2D:
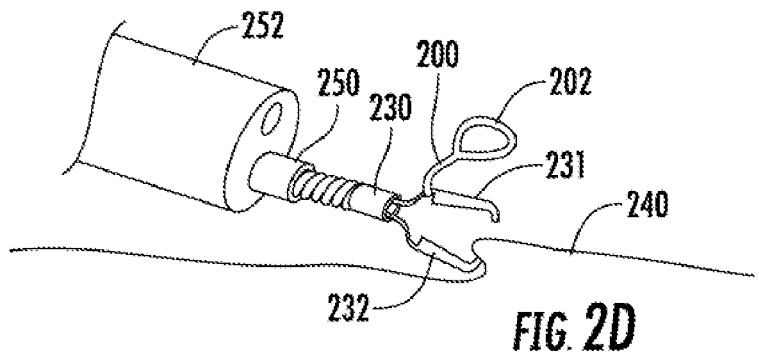
FIG. 2D illustrates the tissue traction device of FIGS. 2A-2C with the clip being oriented toward a target tissue.

With reference to FIG. 2D, the clip 230 may be oriented toward and delivered to a target tissue 240 such that the jaws 231, 232 engage the target tissue 240. An endoscope 252 or other visualization and/or delivery instrument may be used to visualize and orient the sheath 250 and clip 230 toward the target tissue 240. The clip 230 may be positioned (i.e., rotated, extended, etc.) such that the traction band 200 is positioned with the second end 202 of the traction band 200 extending away from the jaws 231, 232 and/or target tissue 240. The traction band 200 may have at least a portion that is stiff enough such that the traction band 200 may support the weight of the second end 202 of the traction band 200 away from the jaws 231, 232, as illustrated in FIG. 2D and in FIG. 2E. In embodiments, the stiffer portion may be integral to the traction band 200, and in other embodiments the stiffer portion may be a separate component attachable to the traction band 200 (such as illustrated in dotted lines in FIG. 2A to schematically indicate a separate stiffer portion along the traction band 200).

Figure 2E:
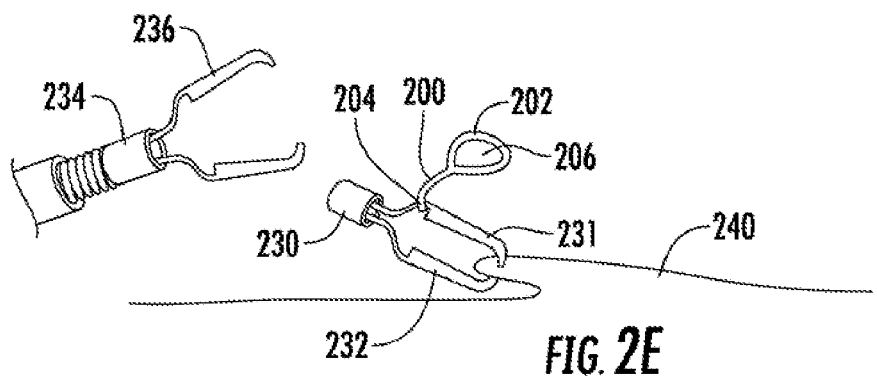
FIG. 2E illustrates the tissue traction device of FIGS. 2A-2D with the clip engaged with the target tissue and a second clip being oriented toward an aperture of the traction band.

With reference to FIG. 2E, the clip 230 is engaging the target tissue 240 such that the second end 202 of the traction band 200 is oriented away from the jaws 231, 232 and the target tissue 240. A second clip 234 is introduced in the vicinity of the target tissue 240. The second clip 234 can orient its jaws 236 toward the second end 202 of the traction band 200 such that the jaws 236 of the second clip 234 can engage the second aperture 206 of the traction band 200. The second aperture 206 is larger than the first aperture 204 such that the second aperture 206 is more easily visible and engageable than the first aperture 204.

Figure 2F:
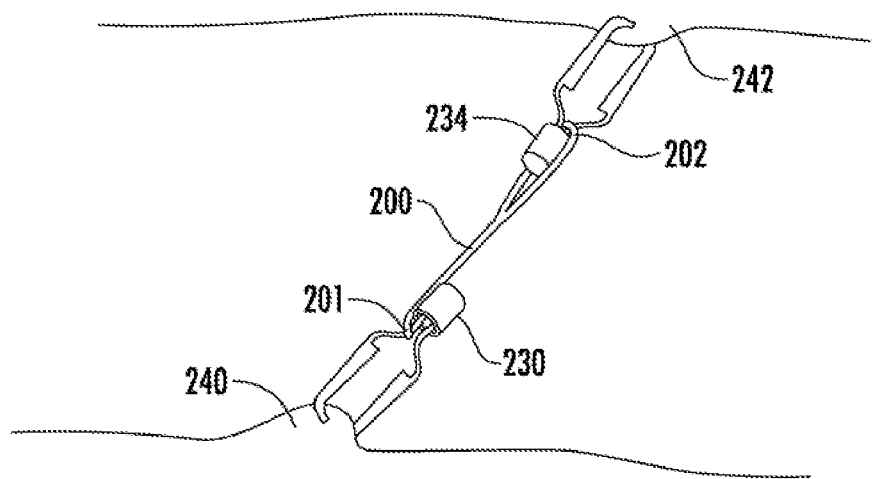
FIG. 2F illustrates the tissue traction device of FIGS. 2A-2E with the second clip engaged with another tissue.

Referring to FIG. 2F, the second clip 234 may be delivered to another tissue 242 while engaged with the second end 202 of the traction band 200. Because the first end 201 of the traction band 200 is substantially fixed with respect to the target tissue 240 via the first clip 230, the traction band 200 can apply tension to the target tissue 240 by the second clip 242 pulling the second end 202 away from the first end 201.

Figure 3A:
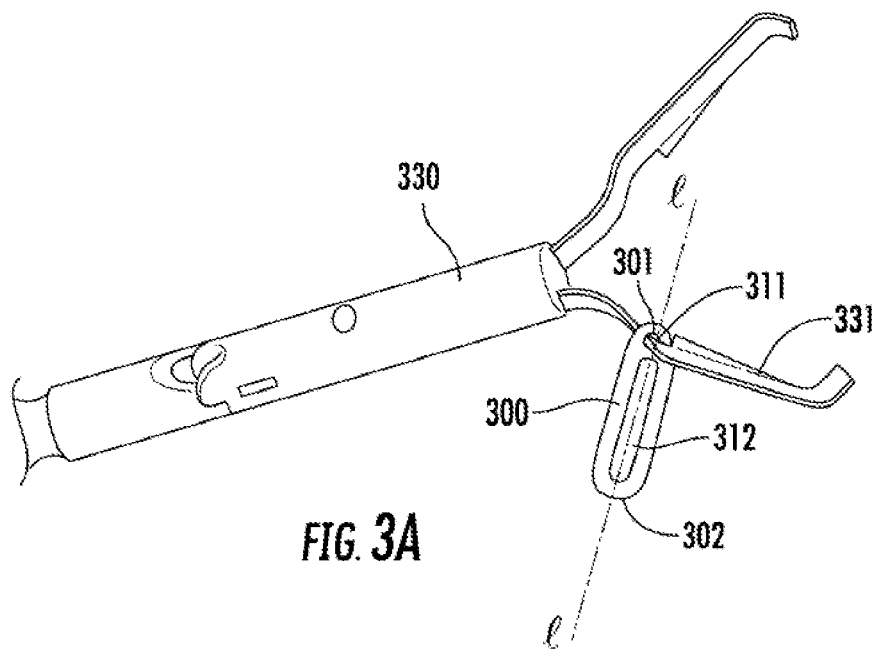
FIG. 3A illustrates a tissue traction device having a traction band disposed on a jaw of a clip, in accordance with an embodiment of the present disclosure.
Figure 3B:
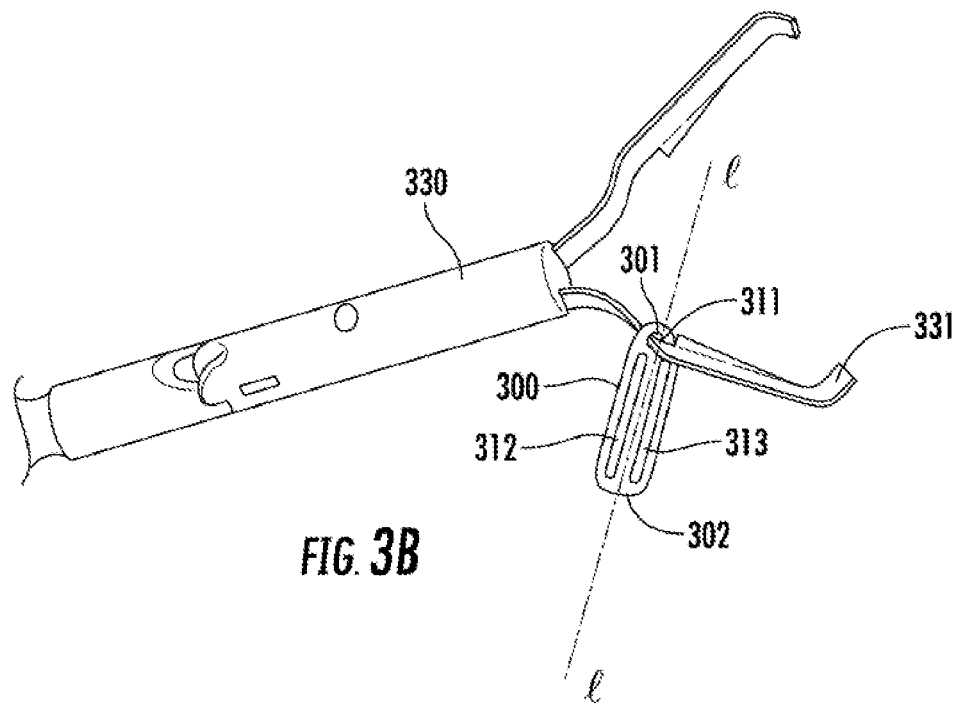
FIG. 3B illustrates a tissue traction device having a traction disposed on a jaw of a clip, in accordance with an embodiment of the present disclosure.
Figure 3C:
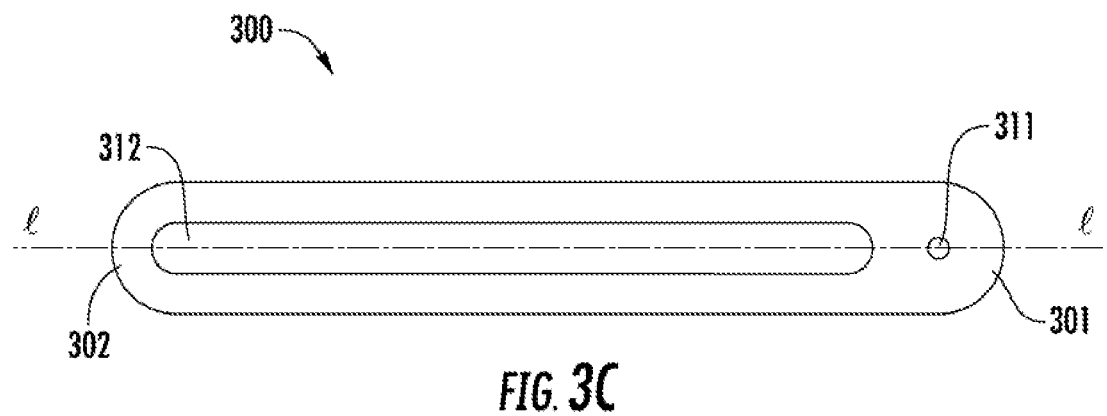
FIG. 3C illustrates a traction band, in accordance with an embodiment of the present disclosure.

Referring to FIGS. 3A and 3B, embodiments of a traction band 300 of a tissue traction device are illustrated including a third aperture 313. A first aperture 311 at a first end 301 of the traction band 300 is disposed about a jaw 331 of the clip 330. A second end 302 of the traction band 300 has a second aperture 312. The second aperture 312 extends along a longitudinal axis $\ell$ of the traction band 300 toward the first aperture 311. The traction band 300 is oriented such that the second end 302 is oriented away from the clip 330. With reference to FIG. 3B, the traction band 300 may also include a third aperture 313. The third aperture 313 extends along the longitudinal axis ℓ of the traction band 300 toward the first aperture 311 and substantially parallel with the second aperture 312. The second and third apertures 312, 313 may be engaged by one or more additional clips or other medical instruments. The length of the second and third apertures 312, 313 extend substantially along the length of the band 300 from the second end 302 to the first end 301 proximate the first aperture 311.

Figure 3D:
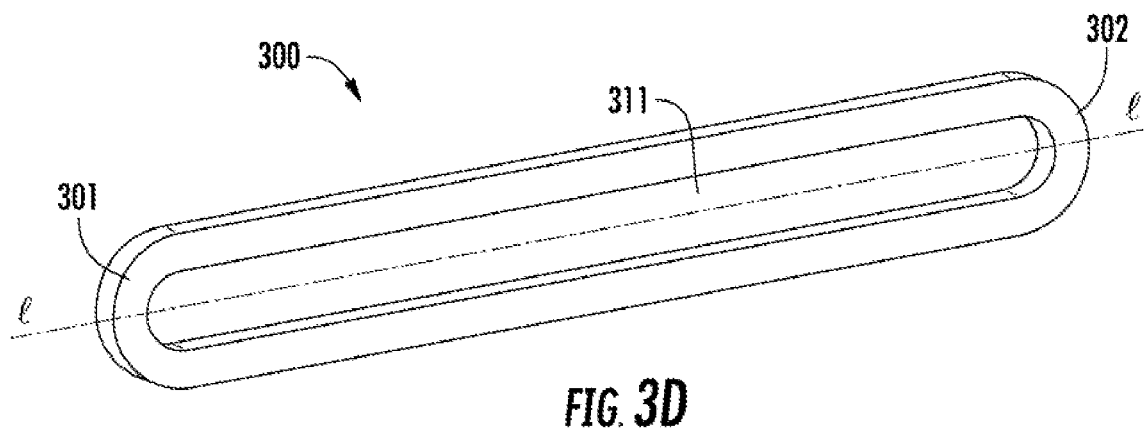
FIG. 3D illustrates a traction band, in accordance with an embodiment of the present disclosure.
Figure 3E:
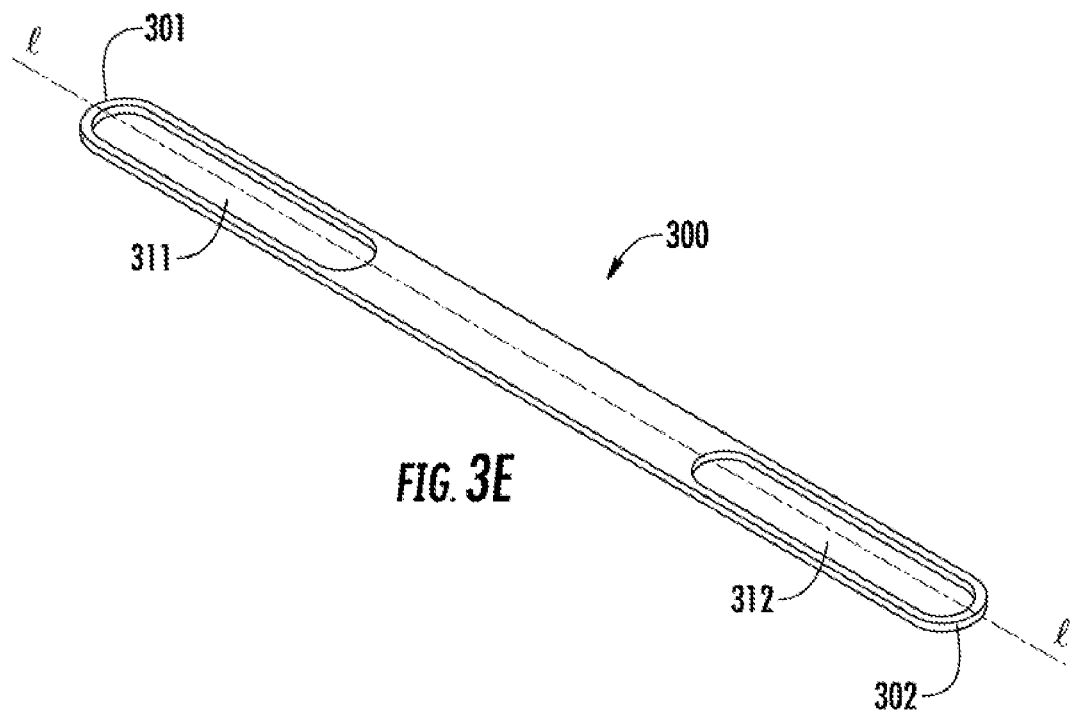
FIG. 3E illustrates a traction band, in accordance with an embodiment of the present disclosure.
Figure 3F:
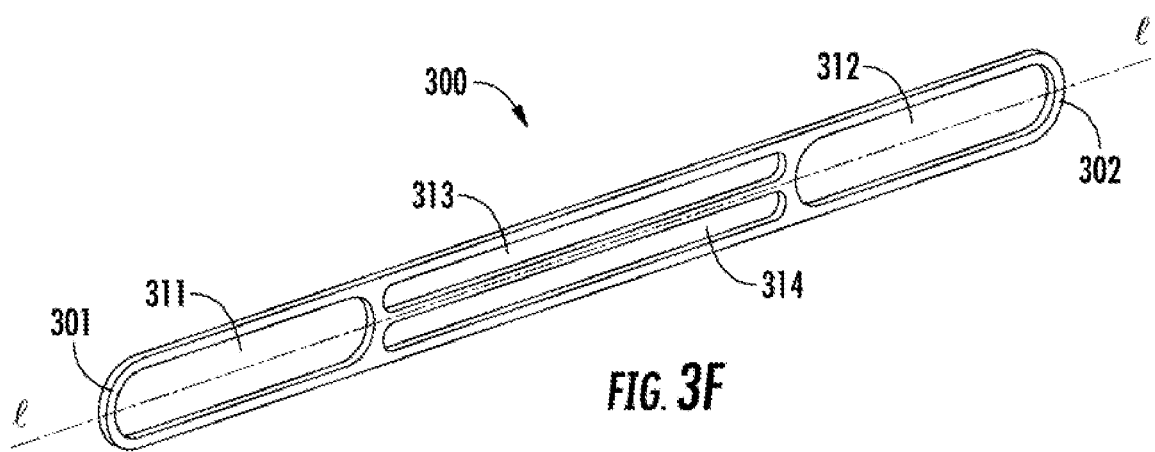
FIG. 3F illustrates a traction band, in accordance with an embodiment of the present disclosure.

With reference to FIGS. 3C-3F, embodiments of tractions bands 300 may include various apertures through the traction band 300. For example, in FIG. 3C, the first aperture 311 may be a substantially circular aperture 311 at the first end 301 of the traction band 300 for receiving at least a portion of a jaw of a first clip. The second aperture 312 may be at the second end 302 of the traction band 300 and extends substantially along the length of the band 300 from the second end 302 to the first end 301 proximate the first aperture 311. The second aperture 312 may be a slot that extends toward the first aperture 312 along the longitudinal axis z,24 of the traction band 300. The first aperture 311 may have a smaller diameter than a diameter of the ends of the slot of the second aperture 312. The first aperture 311 may be used to couple to a first clip by preloading the traction band 300 onto the first clip before a procedure. The second aperture 312 may be engaged by a second clip after the first clip is delivered into the body. In FIG. 3D, the traction band 300 may include only a single aperture 311 extending along the longitudinal axis ℓ of the traction band 300 that may be engaged by one or more clips and may be preloaded attached to one or more clips. In FIG. 3E, the first aperture 311 of the traction band 300 may be at the first end 301 and extend partially along the longitudinal axis ℓ toward the second end 302 of the traction band 300. The second aperture 312 may be at the second end 302 and may partially extend along the longitudinal axis ℓ toward the first end 301. In FIG. 3F, the embodiment of FIG. 3E may further include a third aperture 313 between the first and second aperture 311, 312 extending along the longitudinal axis ℓ. A fourth aperture 314 may extend between the first and second apertures 311, 312 that is substantially parallel with the third aperture 313. Any of the apertures of a traction band 300 may be engaged by a clip and/or additional medical instruments to position, orient, and/or adjust the magnitude or angle of tension in the traction band 300.

Figure 4:
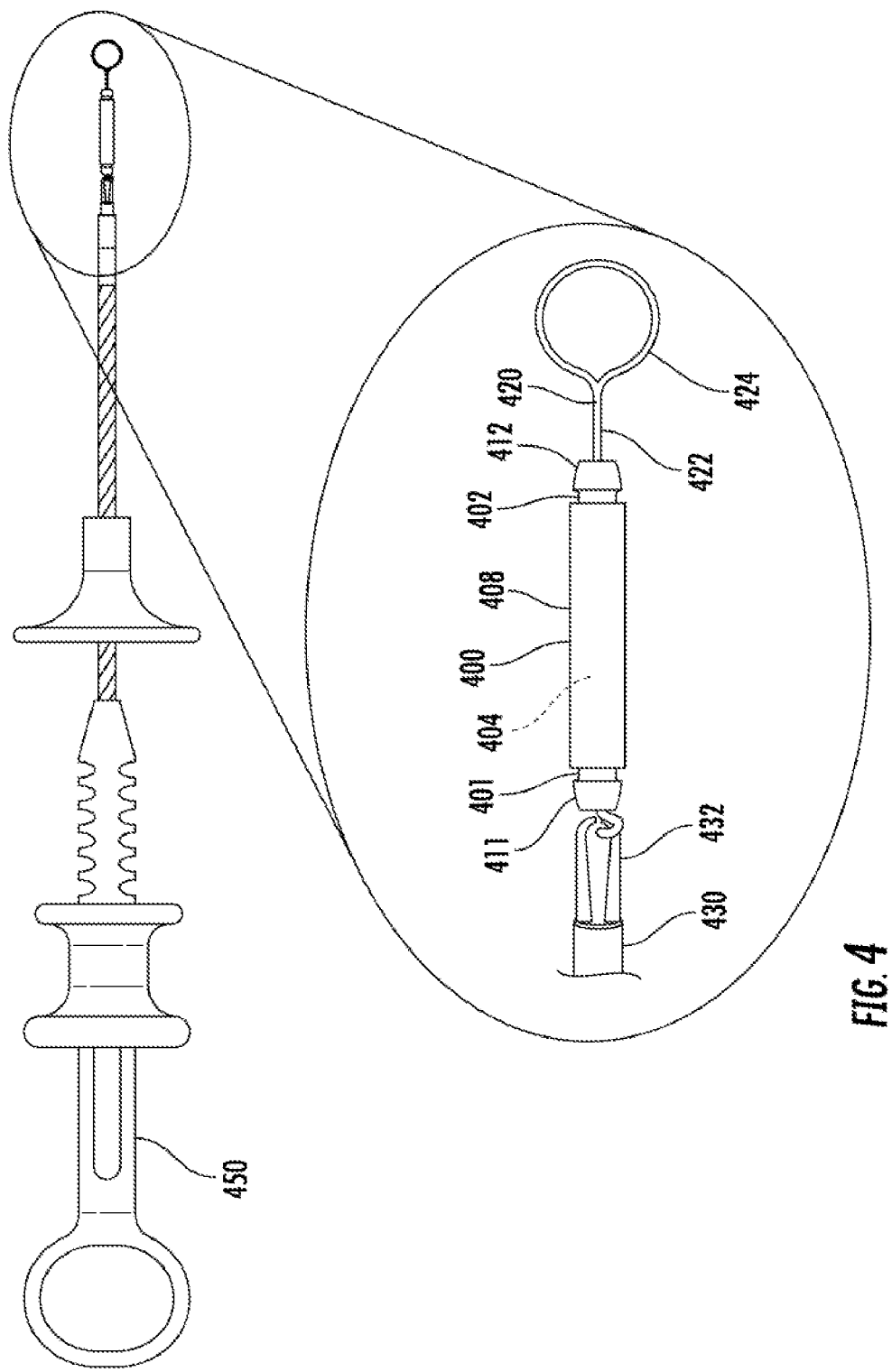
FIG. 4 illustrates a tissue traction device, according to an embodiment of the present disclosure.

Referring to FIG. 4, an embodiment of a traction device is illustrated including a traction band 400 having first 401 and second ends 402. The traction band 400 includes an elastic, stretchable body 404 between the ends 401, 402. An elongate tubular hollow body alignment member 408 is extendable at least partially over the elastic body 404. The alignment member 408 may align and/or orient the traction band 400 within a working channel of a scope, other introducer sheath, or catheter during device manipulation. The alignment member 408 may reduce friction between the elastic body 404 and a working channel. A clip 430, including jaws 432, has one of its jaws 432 coupled to the first end 401 of the traction band 400 via a first connector body 411. A second connector body 412 is coupled to the second end 402 of the traction band 400. A filament 420 extends from the second connector body 412 away from the traction band 400. A loop 424 is formed at an end of the filament 420. The filament 420 extends from the second connector body 412 to the loop 424 by a neck portion 422. The neck portion 422 may extend the loop 424 farther from the connector body 412 such that the loop 424 is easier for a medical professional to visualize and manipulate with an instrument. The tissue traction device may be delivered by a delivery device 450 by the medical professional by operating a handle of the delivery device. The clip 430 may be used by the medical professional to deliver the first end 401 of the traction band 400 that is coupled to the clip 430 to a tissue. The loop 424 may be engaged by another device such as an additional clip. The additional clip may be moved to fix the loop 424 to another anatomy or another portion of the tissue such that the second end 402 of the traction band 400 extends away from the first end 401. In this position, the traction band 400 is placed in greater axial tension compared to a relaxed state of the traction band 400 that is illustrated in FIG. 4. The tissue traction device of FIG. 4 may be used substantially similar to that of FIG. 1 discussed above.

Figure 5A:
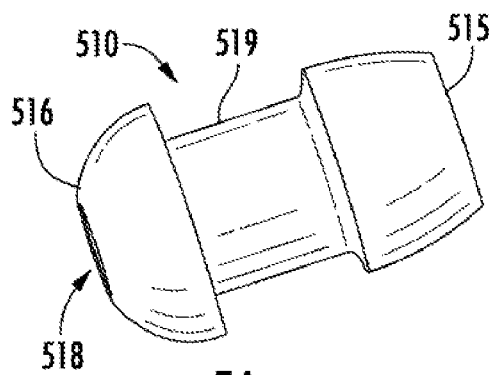
FIG. 5A illustrates a connector body, in accordance with an embodiment of the present disclosure.

Referring to FIG. 5A, an embodiment of a connector body 510 (which may alternately be referenced as a bobbin, without intent to limit) is illustrated having a first end 515, a second end 516, and a lumen 518 therethrough. The connector body 510 has a larger diameter at the second end 516 than at the first end 515. A traction band and/or an alignment member may have an outer diameter larger than the first end 515 and smaller than the second end 516 such that the traction band and/or alignment member may couple to the connector body 510 by being disposed about the first end 515 but not extending past the second end 516. The connector body 510 includes a saddle region 519 having a smaller diameter than that of the first end 515 and the second end 516. The saddle region 519 may provide a region for a traction band and/or an alignment member to frictionally couple to the connector body 510 (e.g., between the saddle region 519 and the first end 515, along a portion of or the entirety of the saddle region 519, the saddle region 519 may be a region for the application of adhesive to join the connector body to the traction band or alignment member, etc.). The second end 516 may include an atraumatic curved surface that may reduce friction with working channels, devices, or anatomies compared to an edge. A connector body 510 may be rotatably coupled to a traction band, e.g., with an aperture, a cavity, or a lumen of a traction band, such that the connector body 510 may rotate freely about a longitudinal axis of the connector body 510 and/or the traction band such that there is minimal twisting of the traction band.

Figure 5B:
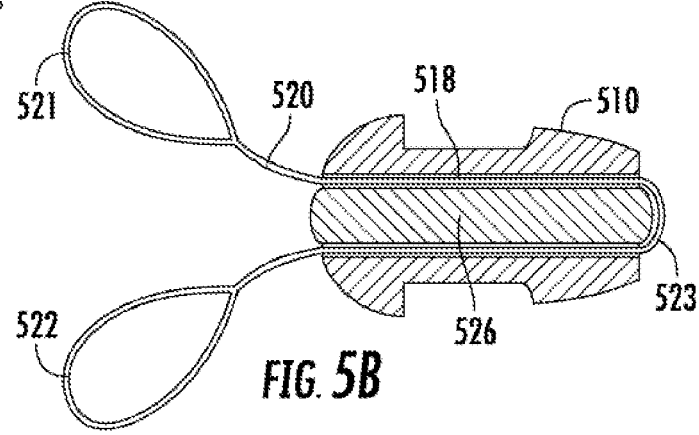
FIG. 5B illustrates a cross-sectional view of a connector body with a filament, in accordance with an embodiment of the present disclosure.
Figure 5C:
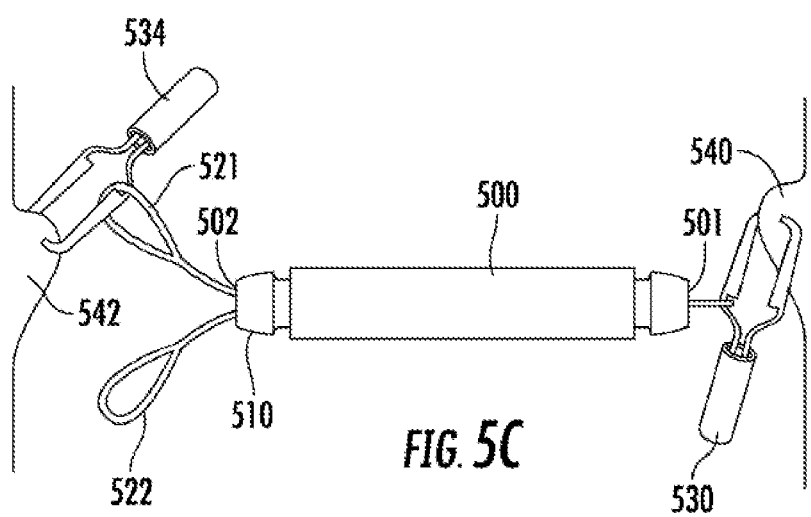
FIG. 5C illustrates a tissue traction device including connector bodies delivered into a body lumen, in accordance with an embodiment of the present disclosure.

With reference to FIG. 5B, a cross-sectional view of an embodiment of a connector body 510 is illustrated including a lumen 518. A filament 520 having a loop at each of a first end 521 of the filament 520 and a second end 522 of the filament 520 is disposed within the lumen 518. The filament includes a midportion 523 extending through the lumen 518. The first and second ends 521, 522 of the filament 520 extend outside of the lumen 518 on the same side of the connector body 510. A cannula 526 dimensioned to compliment the lumen 518 (e.g., substantially similar diameters and lengths depending on a desired fit) is slidingly disposed within the lumen 518. The cannula 526 temporarily couples the midportion 523 of the filament 520 within the lumen 518 by the midportion 523 extending along the cannula 526 within the lumen 518. The at least part of the midportion 523 may be pinched between the cannula 526 and the connector body 510 within the lumen 518. With reference to FIG. 5C, the connector body 510 may be coupled to a traction band 500. In use, a first end 501 of the traction band 500 may be coupled to a target tissue 540 by a first clip 530 while a second end 502 of the traction band 500 may be coupled to another tissue portion 542 by a second clip 534. The second clip 534 may couple the traction band 500 to the other tissue portion 540 by engaging a loop at the first end 521 of the filament. In this position, a loop at the second end 522 may be left freely hanging from the connector body 510. The traction band 500 may be extended between the target tissue 540 and the other tissue portion 542 as described throughout the disclosure. The cannula 526 coupling the midportion 523 of the filament 520 to the connector body 510 may fit tightly enough within the lumen 518 such that the traction band 500 may be tensioned without uncoupling the cannula 526 and midportion 523 from the lumen 518. The filament 523 may be uncoupled from the connector body 510 by an instrument engaging the loop of the second end 522 of the filament 520 and pulling on the second end 522 such that the fixed first end 521 and tensioned second end 522 dislodge the cannula 526 and midportion 523 from the lumen 518. The portions of the filament 520 extending between the ends 521, 522 and the lumen 518 may be substantially equal in length or may differ in length from each other. Varying lengths of these portions of the filament 520 may allow a physician to choose a preferred length for attaching one of the ends 521, 522 to an anatomy. The devices may be left within the body to be passed naturally, or some or all of the devices may be removed from the body after a procedure.

Figure 5D:
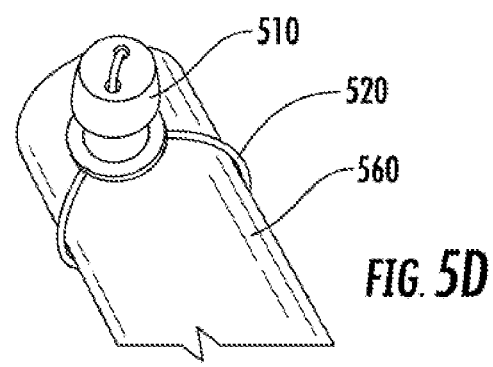
FIG. 5D illustrates filament of a connector body being formed into a loop about a mandrel, in accordance with an embodiment of the present disclosure.

With reference to FIG. 5D, an embodiment of a connector body 510 is illustrated with a filament 520 extending from the connector body 510. The portion of the filament 520 outside of the connector body 510 is being formed into a loop about a mandrel 560.

Figure 6A:
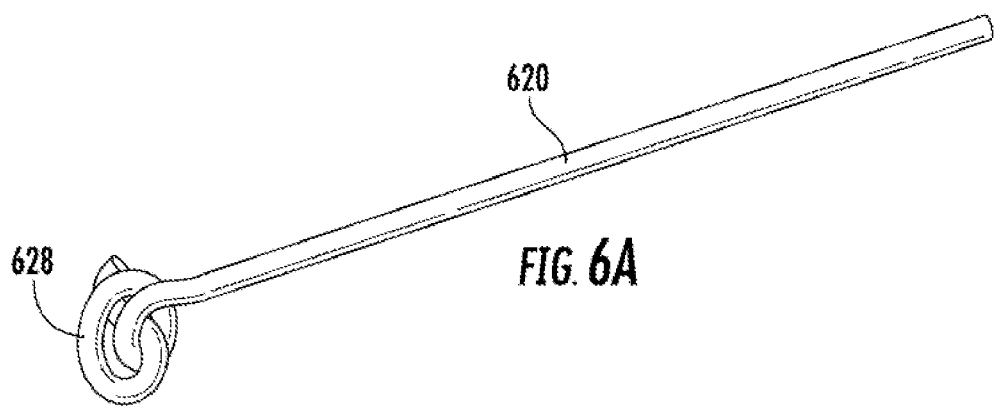
FIG. 6A illustrates a filament with a knot, in accordance with an embodiment of the present disclosure.
Figure 6B:
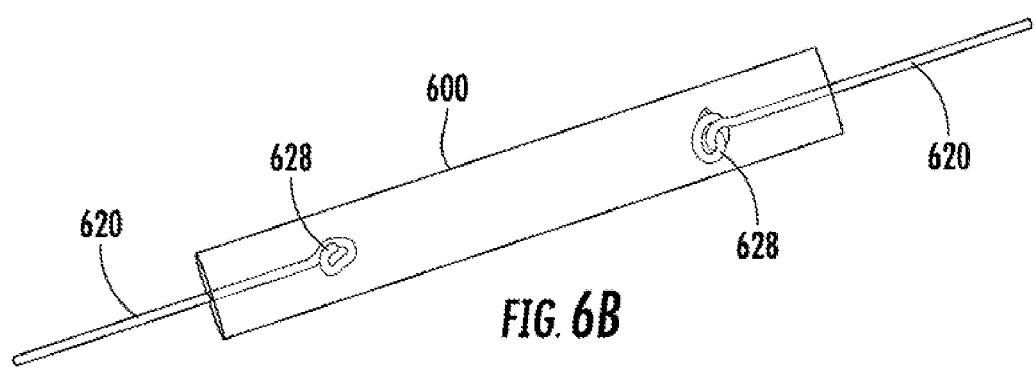
FIG. 6B illustrates a traction band with filaments extending from ends of the traction band, in accordance with an embodiment of the present disclosure.
Figure 6C:
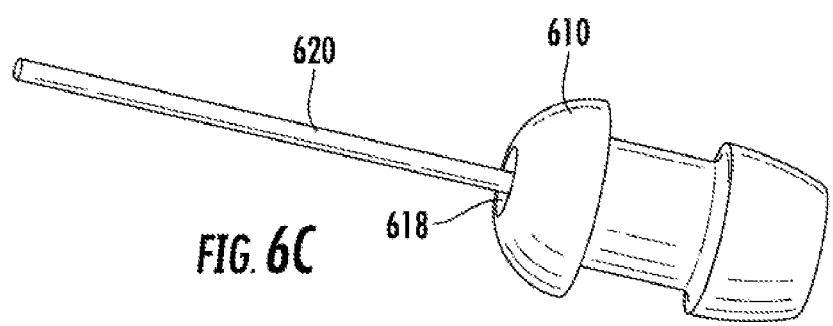
FIG. 6C illustrates a filament extending out of a connector body.

Referring to FIGS. 6A-6G, embodiments of a filament 620 may be coupled to a device in various ways. FIG. 6A illustrates a filament 620 having a knot 628 at an end that may be tied to, embedded within, or provide a bulbous stop against a device. FIG. 6B illustrates a traction band 600 with two filaments 620 extending from each end of the traction band 600. The filaments each include a knot 628 embedded within the traction band 600. One or more knots 628 of a filament 620 may be embedded within a traction band 600, e.g., by overmolding the traction band 600 about the knots 628. FIG. 6C illustrates a connector body 610 with a filament 620 extending out of a lumen 618 of the connector body 610. The filament 620 may be coupled to the connector body 610, e.g., by a knot. FIG. 6D illustrates a connector body 610 with a midportion 623 of a filament 620 extending through a lumen 618 of the connector body 610. The midportion 623 is coupled to an anchoring element 629 having a diameter larger than a diameter of at least a section of the lumen 618 such that the anchoring element 629 coupled to the midportion cannot translate through the lumen 618. The midportion 623 may be tied, looped, welded, or otherwise adhered to the anchoring element 629. FIG. 6E illustrates an end of a filament 620 with a bulbous body 627 coupled to the filament 620. The bulbous body 627 may be larger than a diameter of an aperture or lumen of another device such that the bulbous body 627 may anchor the filament 620 to the device. The bulbous body 627 may be coupled to the filament 620 by crimping, melting, welding, or otherwise adhering the bulbous body 627 to the filament 620. FIG. 6F illustrates an end of a filament 620 having a bulbous portion 626. The bulbous portion 626 may be larger than a diameter of an aperture or lumen of another device such that the bulbous portion 626 may anchor the filament 620 to the device. The bulbous portion 626 may be formed by at least partially melting the filament such that it forms into a larger diameter bulbous portion 626 and/or additional material may be formed about the filament 620. It will be appreciated that the proportions of the bulbous portion 626 may differ from those illustrated. For instance, the bulbous portion may have a length substantially equal to the width thereof. A clip may be coupled to a filament end (that may include a loop) by the filament extending through an aperture in a jaw of the clip. For example, FIG. 6G illustrates a clip 630 with an aperture 635 through one of the jaws 631 of the clip 630. A filament 620 having a bulbous portion 626 is extending through the aperture 635. The bulbous portion 626 has a wider diameter than the aperture 635 such that the filament 620 cannot be pulled out of the aperture 635 in at least one direction without applying enough force to deform the bulbous body 626.

Figure 7:
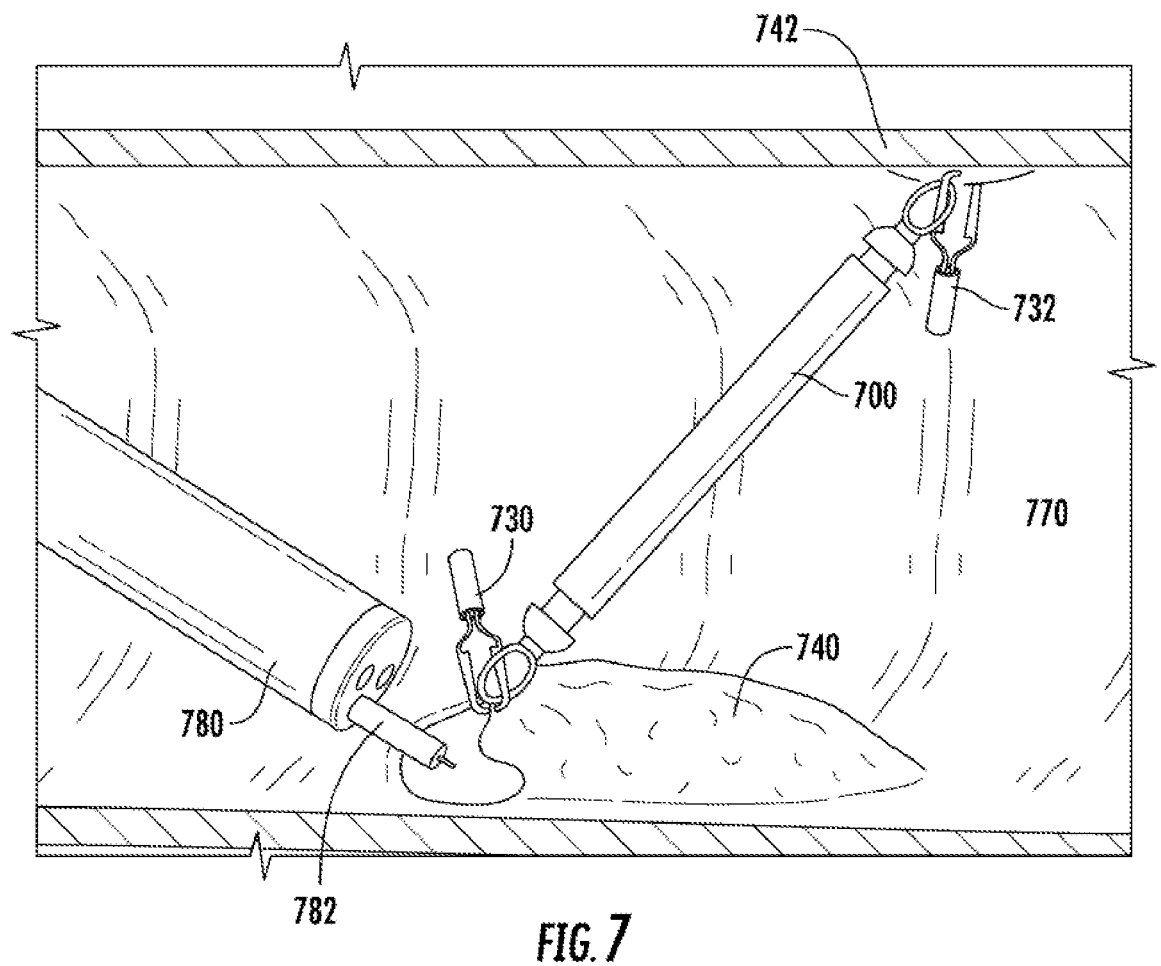
FIG. 7 illustrates a tissue traction device delivered within a body lumen, in accordance with an embodiment of the present disclosure.

Referring to FIG. 7, an embodiment of a tissue traction system is illustrated within a body lumen 770. A traction band 700 is attached to a target tissue 740 at one end by a first clip 730 and the traction band 700 is attached to another portion of tissue 742 of the body lumen 770 at a second end by a second clip 732. The traction band 700 may assist a medical professional that is operating a cutting instrument 782 to resect the target tissue 740 by applying tension to the target tissue 740 such that the medical professional may more easily access the perimeter of the target tissue with the cutting instrument 782 and/or more easily visualize the anatomy or devices, e.g., via a scope 780. A tension in the traction band 700 may be adjusted if the target tissue 740 and the other tissue portion 742 of the body lumen 770 are moved in relation to each other. Tension may be increased by insufflating the body lumen 770 with a fluid (e.g., atmospheric air, $CO_2$, or the like through a working channel of the scope 780) such that the volume of the body lumen increases, separating the target tissue 740 from the other tissue portion 742 and thereby increasing tension in the traction band 700. Tension may be decreased by suctioning or passively ventilating fluid or gas (atmospheric air, $CO_2$, etc.) from the body lumen 770 (e.g., through a working channel of the scope 780) such that the volume of the body lumen decreases, bringing the target tissue 740 closer to the other tissue portion 742 and thereby decreasing tension in the traction band 700. Either insufflation or suction may be employed to a body lumen before, during, or after a traction device is delivered.

In various embodiments, a clip may be rotatable to rotate or rotate about a traction band. A clip may be repositionable before, during, and/or after a procedure. A clip may be a single use clip (i.e., not repositionable). A medical procedure such as resecting of a tissue may be performed with a traction device coupled to one or more tissues in tension. During and/or after the procedure, tension may be released by severing a portion of the device, such as a filament, a traction band, an alignment member, a neck portion, and/or a loop. Examples of tissue traction devices and associated instruments may include, but are not limited to, those described in U.S. Provisional Patent Application No. 62/923,042, filed Oct. 18, 2019, and titled "Filament Cutting Devices, Systems, and Methods," and U.S. Pat. No. 11,980, 355, issued May 14, 2024, and titled "Tissue Traction Bands and Methods for Tissue Traction," each of which are herein incorporated by reference in their entirety and for all purposes.

In various embodiments, a traction device may include no filaments, one filament, or multiple filaments. A traction band may include an internal filament extending between ends of a traction band that may prevent the traction band from stretching beyond a desirable length. A filament of a traction device may comprise, extend to, or be coupled to one or more loops that can be various shapes and diameters.

In various embodiments, a filament may comprise various shapes such as a loop, a hook, an anchor, a knot, a barb, an eyelet, a combination thereof, or the like. In various embodiments, a filament may comprise a polymer strand (e.g., polypropylene, polyester, nylon, polyethylene, elastic polymers including thermoplastic elastomer (TPE), polyisoprene, silicone, and/or the like), a metal wire (e.g., stainless steel, titanium, cobalt-chrome, nitinol, and/or the like), and/or a natural fiber (e.g., cotton, wool, silk, and/or the like). A filament may have a material strength configured to fail at a pre-determined load as a safety feature to limit an amount of tension in the traction band and the surrounding tissue. One or more filaments may be visually marked such that the filaments are visually distinguishable with respect to other filaments. For example, the filaments may vary in colors, patterns, or radiopacity such that a medical professional can easily identify a selected filament meant for fixation to a target tissue, an anchoring tissue, a second anchoring tissue, for releasing from a connector body, etc.

In various embodiments, a traction band and/or an elastic body of a traction band may comprise a compliant or semi-compliant material (e.g., thermoplastic elastomer (TPE), REZILIENT™ Rx15A, MEDALIST™ MD-16110, polyethylene terephthalate (PET), elastic polymers, rubbers, plastics, etc.). The traction band may be an elongate cylindrical tube and may be formed hollow or solid. Materials may be elastic with a lower durometer and lower tensile modulus compared to materials of other devices involved with a medical procedure. A transparent or opaque material may be used.

In various embodiments, some steps of assembling a tissue traction device may occur outside of the patient's body, while other steps involved in assembling the tissue traction device may occur within the patient. The steps described herein do not necessarily occur in a specific order and/or timing.

The medical instruments used with various embodiments of the devices, systems, and methods herein are not limited to those illustrated and discussed but may include a variety of medical instruments (e.g., ablative elements, biopsy needles, injection needles, scissors, graspers, clips, etc.).

In various embodiments, an access area beneath and about a target tissue to be resected by a medical professional may be visualized. Visualization may be optical, fluoroscopic, ultrasonic, etc. The visualization of the area beneath and about the target tissue may not be adequately revealed for the medical professional to manipulate a medical instrument to the access area to resect the target tissue. The medical professional may deliver and deploy a tissue traction device or system to the target tissue and an anchoring tissue at a length and/or at a tension that reveals the access area for the procedure. The medical professional may adjust the length or tension of the system based on visualization of the target tissue or access area.

In various embodiments, filament may be engaged with a variety of different fasteners configured to engage a tissue traction device to a tissue, such as a clip, an anchor, a screw, a pin, or the like. For example, a clip contemplated for use with a tissue traction device may include a biased-open configuration configured to move to a closed/clamped configuration upon actuation by a handle assembly. In addition, or alternatively, a tissue clip contemplated for use with a disclosed tissue traction device may include a biased-closed configuration configured to move an open configuration upon actuation of a distal end effector (e.g., squeezing) by a proximal handle assembly. In addition, or alternatively, fasteners other than detachable/releasable tissue clips may be used to secure/engage the attachment members of the disclosed tissue traction device to the wall of a body lumen, such as non-repositionable clips. Examples of fasteners may include, but are not limited to, those described in U.S. patent application Ser. No. 15/930,604, filed May 13, 2020, and titled "Tissue Clip Devices, Systems, and Traction Methods," U.S. patent application Ser. No. 16/668,341, filed Oct. 30, 2019, and titled "Clip Devices, Systems, and Methods for Engaging Tissue," and in U.S. Patent Application Publication number US2018/0263614, filed Mar. 19, 2018, published Sep. 20, 2018, and titled "Tissue Retraction Device and Delivery System," all of which are herein incorporated by reference in their entirety and for all purposes.

In various embodiments, a method of retracting tissue may include delivering a tissue traction device to a target tissue. A first filament and/or connector body extending from a first end of a traction band may be attached to the target tissue. A second filament and/or connector body extending from a second end of the traction band device may be attached to another portion of tissue. The target tissue may be resected. A tension, and/or length of the tissue traction device, applied by the tissue traction device to the target tissue may be adjusted. One or more filaments and the target tissue may be engaged by a clip. One or more filaments and the other tissue portion may be engaged by a clip. An area of access beneath the target tissue may be visualized and a position of any of the devices may be adjusted based on the visualized area of access.

In various embodiments, a method of resecting a target tissue may include coupling a first end of a traction band to the target tissue. A second end of the traction band may be coupled to another tissue. A body lumen comprising the target tissue may be insufflated thereby increasing a tension in the traction band. The target tissue may be resected. The body lumen may be suctioned thereby decreasing a distance between the target tissue and the other tissue. The body lumen may be ventilated thereby decreasing a distance between the target tissue and the other tissue. A midportion of the traction band may be coupled to a third tissue. The traction band may be released from the other tissue.

All of the devices and/or methods disclosed and claimed herein can be made and executed without undue experimentation in light of the present disclosure. While the devices and methods of this disclosure have been described in terms of preferred embodiments, it may be apparent to those of skill in the art that variations can be applied to the devices and/or methods and in the steps or in the sequence of steps of the method described herein without departing from the concept, spirit and scope of the disclosure. All such similar substitutes and modifications apparent to those skilled in the art are deemed to be within the spirit, scope and concept of the disclosure as defined by the appended claims.

What is claimed is:

1. A tissue traction device, comprising:
   a first clip comprising opposable jaws;
   a stretchable traction band having a first end and a second end the stretchable traction band comprising:
      a first aperture formed in the first end of the stretchable traction band; and
      a second aperture formed in the second end of the stretchable traction band;
      and an elongated length extending between the first aperture and the second aperture and without having apertures extending therethrough;
   wherein:
   a first jaw of the opposable jaws of the first clip is disposed through the first aperture; and the first aperture is sized to connect the stretchable traction band to the first jaw by a friction fit.

2. The tissue traction device of claim 1, wherein the second aperture extends along the longitudinal axis toward the first aperture.

3. The tissue traction device of claim 1, wherein the second aperture has a diameter that is larger than an outer diameter of the first end of the stretchable traction band.

4. The tissue traction device of claim 1, wherein the second end of the stretchable traction band is extendable away from a second jaw of the opposable jaws in a deployed configuration.

5. The tissue traction device of claim 1, further comprising a second clip at least partially disposable through the second aperture.

6. The tissue traction device of claim 1, wherein the first jaw of the first clip further comprises a wall extending substantially radially from the first jaw adjacent the stretchable traction band.

7. The tissue traction device of claim 1, wherein the elongated length of the stretchable traction band extending between the first aperture and the second aperture has a portion stiff enough to support the weight of the second end of the stretchable traction band away from the first end of the stretchable traction band.

8. The tissue traction device of claim 7, wherein the stiff portion is integral to the stretchable traction band.

9. The tissue traction device of claim 7, wherein the stiff portion is a separate component attachable to the stretchable traction band.

10. A method of resecting a target tissue, comprising:
- coupling a first end of an elongated stretchable traction band to the target tissue with a first clip having a jaw connected through an aperture formed in the first end of the traction band by a friction fit;
- coupling a second end of the traction band, spaced apart from the first end by an elongated length without apertures therethrough, to another tissue with a second clip;
- insufflating a body lumen in which the target tissue is located to increase a tension in the traction band; and
- resecting the target tissue.

11. The method of resecting a target tissue of claim 10, further comprising suctioning the body lumen thereby decreasing a distance between the target tissue and the other tissue.

12. The method of resecting a target tissue of claim 10, further comprising ventilating the body lumen thereby decreasing a distance between the target tissue and the other tissue.

13. The method of resecting a target tissue of claim 10, coupling a midportion of the traction band to a third tissue.

14. The method of resecting a target tissue of claim 10, further comprising releasing the traction band from the other tissue.

15. A tissue traction device, comprising:
- an elongated traction band having a first end and a second end, the traction band comprising:
- a first aperture formed in the first end of the traction band and having an inner diameter;
- a second aperture formed in the second end of the traction band and having an inner diameter larger than the inner diameter of the first aperture; and
- an elongated length without apertures therethrough extending between and spacing apart the first aperture and the second aperture.

16. The tissue traction device of claim 15, wherein the first aperture is sized to form a friction fit with the jaw of a tissue clip extended therethrough.

17. The tissue traction device of claim 16, wherein the second end of the elongated traction band is extendable away from the jaw of the tissue clip in a deployed configuration.

18. The tissue traction device of claim 15, wherein the second aperture has a diameter that is larger than an outer diameter of the first end of the traction band.

19. The tissue traction device of claim 15, wherein the elongated length of the elongated traction band extending between the first aperture and the second aperture has a portion stiff enough to support the weight of the second end of the elongated traction band away from the first end of the elongated traction band.

20. The tissue traction device of claim 19, wherein the stiff portion is a separate component attachable to the stretchable traction band.

* * * * *